United States Patent
Shusterman

(10) Patent No.: US 7,343,197 B2
(45) Date of Patent: *Mar. 11, 2008

(54) MULTI-SCALE ANALYSIS AND REPRESENTATION OF PHYSIOLOGICAL AND HEALTH DATA

(76) Inventor: Vladimir Shusterman, 245 Melwood Ave., Apt. 501, Pittsburgh, PA (US) 15213

( * ) Notice: Subject to any disclaimer, the term of this patent is extended or adjusted under 35 U.S.C. 154(b) by 743 days.

This patent is subject to a terminal disclaimer.

(21) Appl. No.: 10/816,638

(22) Filed: Apr. 2, 2004

(65) Prior Publication Data
US 2004/0193064 A1 Sep. 30, 2004

Related U.S. Application Data

(63) Continuation-in-part of application No. 10/124,651, filed on Apr. 17, 2002, now Pat. No. 6,925,324, which is a continuation-in-part of application No. 09/583,668, filed on May 30, 2000, now Pat. No. 6,389,308.

(51) Int. Cl.
*A61B 5/0402* (2006.01)

(52) U.S. Cl. .................................... 600/509

(58) Field of Classification Search ......... 600/508–521
See application file for complete search history.

(56) References Cited

U.S. PATENT DOCUMENTS

| | | | |
|---|---|---|---|
| 4,193,393 | A | 3/1980 | Schlager |
| 4,679,144 | A | 7/1987 | Cox et al. |
| 5,033,475 | A | 7/1991 | Ueda et al. |
| 5,501,229 | A | 3/1996 | Selker et al. |
| 5,724,983 | A | 3/1998 | Selker et al. |
| 5,956,013 | A | 9/1999 | Raj et al. |
| 5,967,995 | A | 10/1999 | Shusterman et al. |
| 6,038,469 | A | 3/2000 | Karlsson et al. |

OTHER PUBLICATIONS

V. Shusterman and O. Trofimov, Building and Application of Expert Systems for Differential Diagnostics of Cardiovascular Diseases; SAMS, 1994, vol. 14, pp. 15-24.

William G. Baxt, MD et al., A Neural Network Aid for the Early Diagnosis of Cardiac Ischemia in Patients Presenting to the Emergency Department With Chest Pain, Annals of Emergency Medicine, Dec. 2002, pp. 575-583.

Hongmei Yan et al., The internet-based knowledge acquisition and management method to construct large-scale distributed medical expert systems, Computer Methods and Programs in Biomedicine (2004) 74, pp. 1-10.

*Primary Examiner*—Scott M. Getzow
(74) *Attorney, Agent, or Firm*—David V. Radack; Eckert Seamans Cherin & Mellott, LLC

(57) ABSTRACT

System comprised of a medical device and method for analyzing physiological and health data and representing the most significant parameters at different levels of detail which are understandable to a lay person and a medical professional. Low, intermediate and high-resolution scales can exchange information between each other for improving the analyses; the scales can be defined according to the corresponding software and hardware resources. A low-resolution Scale I represents a small number of primary elements such as intervals between the heart beats, duration of electrocardiographic PQ, QRS, and QT-intervals, amplitudes of P-, Q-, R-, S-, and T-waves. This real-time analysis is implemented in a portable device that requires minimum computational resources. The set of primary elements and their search criteria can be adjusted using intermediate or high-resolution levels. At the intermediate-resolution Scale II, serial changes in each of the said elements can be determined using a mathematical decomposition into series of basis functions and their coefficients. This scale can be implemented using a specialized processor or a computer organizer. At the high-resolution Scale III, combined serial changes in all primary elements can be determined to provide complete information about the dynamics of the signal. This scale can be implemented using a powerful processor, a network of computers or the Internet. The system can be used for personal or group self-evaluation, emergency or routine physiological monitoring and analysis, or continuous event, stress test or bedside physiological monitoring.

59 Claims, 10 Drawing Sheets

| Scale I | | | | |
|---|---|---|---|---|
| Heart Rate<br>A<br>43 | Beat<br>N<br>sinus | Axis<br>N<br>60 | PR-interval<br>N<br>0.15 | P-amplitude<br>N<br>0.03 |
| QRS-duration<br>N<br>0.1 | Q-amplitude<br>N<br>0.2 | R-amplitude<br>N<br>0.8 | S-amplitude<br>N<br>0.2 | T-amplitude<br>N<br>0.3 |
| ST-segment<br>N<br>0.0 | QT-interval<br>N<br>0.4 | | | |

| Scale I | | | | |
|---|---|---|---|---|
| Heart Rate<br>C<br>63 | Beat<br>U<br>sinus | Axis<br>U<br>60 | PR-interval<br>U<br>0.15 | P-amplitude<br>U<br>0.03 |
| QRS-duration<br>U<br>0.1 | Q-amplitude<br>U<br>0.2 | R-amplitude<br>U<br>0.8 | S-amplitude<br>U<br>0.2 | T-amplitude<br>U<br>0.3 |
| ST-segment<br>U<br>0.0 | QT-interval<br>U<br>0.4 | | | |

FIG. 4

| Scale I | | | | |
|---|---|---|---|---|
| Heart Rate<br>N<br>67 | Beat<br>N<br>sinus | Axis<br>N<br>50 | PR-interval<br>N<br>0.12 | P-amplitude<br>N<br>0.014 |
| QRS-duration<br>N<br>0.11 | Q-amplitude<br>A<br>0.38 | R-amplitude<br>N<br>1.0 | S-amplitude<br>N<br>0.2 | T-amplitude<br>N<br>0.1 |
| ST-segment<br>N<br>0.0 | QT-interval<br>A<br>0.58 | | | |

| Scale I | | | | |
|---|---|---|---|---|
| Heart Rate<br>U<br>67 | Beat<br>U<br>sinus | Axis<br>U<br>50 | PR-interval<br>U<br>0.12 | P-amplitude<br>U<br>0.014 |
| QRS-duration<br>U<br>0.11 | Q-amplitude<br>U<br>0.38 | R-amplitude<br>U<br>1.0 | S-amplitude<br>U<br>0.2 | T-amplitude<br>C<br>-0.35 |
| ST-segment<br>C<br>-0.02 | QT-interval<br>U<br>0.58 | | | |

FIG. 10

MULTI-SCALE ANALYSIS AND REPRESENTATION OF PHYSIOLOGICAL AND HEALTH DATA

CROSS-REFERENCE TO RELATED APPLICATION

This is a continuation-in-part of application Ser. No. 10/124,651, filed Apr. 17, 2002, now U.S. Pat. No. 6,925,324 which was a continuation-in-part of application Ser. No. 09/583,668, filed May 30, 2000, now U.S. Pat. No. 6,389,308.

FIELD OF THE INVENTION

This invention relates to the field of methods and apparatus for analyzing physiological data and its serial changes, including small changes that cannot be exposed by conventional analysis, structuring and representing the results in the form understandable both to lay public and medical professionals, and to the implementation of such methods and apparatus using a distributed network of personal and centralized communication devices.

BACKGROUND OF THE INVENTION

Registration of physiological data is relatively simple, however, the subsequent processing and analysis are complex and require highly qualified medical personnel.

In general, there are two types of ECG tests, a one-time recording during a few seconds and a long-term monitoring which can be performed during various physiological tests, regular daily activities or as a round-the-clock monitoring in patients with serious medical disturbances. Each test requires a specialized protocol for registering and analyzing ECG signals.

One-time ECG recording is usually performed by ECG technicians or paramedics. The recording then is transferred to a physician for analysis, which includes a number of procedures. First, the cardiac complexes are visually identified by their characteristic shape consisting of a sequence of the following waves: P-, Q-, R-, S-, T- and sometimes U-wave. Next, these complexes are classified according to their origin as normal or sinus, supraventricular, ventricular complexes and their subtypes. The distance between two consecutive complexes is measured to determine the heart rate. Next, a number of the most important parameters including the amplitudes of each wave, the duration of PQ, QRS, and QT-intervals, and the amplitude of ST-segment are measured. Finally, the signals are compared with the recordings that were previously obtained from the same patients to determine serial changes in cardiac electrical activity.

Comparison of serial recordings is an important part of standard ECG examination that allows detection of changes and determining their time course. The comparison is performed visually by an experienced medical professional. The accuracy of this subjective comparison is not high and varies among physicians. The accuracy is not stable even in the same physician when the same measurements are repeated several times.

There are a number of prior art computerized systems that follow these basic steps of analysis and measure characteristic waves of ECG and prepare preliminary report for physicians. Since the number of analyzed variables and their combinations is large, these systems use sophisticated processing algorithms that require fast and powerful microprocessors or computers with a large memory available for processing.

Systems for long-term monitoring consist of two types, recording and real-time systems. Recording systems include 24-hour Holter monitors and event monitors, which record the data after a manual signal (event). Processing of these recordings, which include a large amount of data, consists of computer-assisted scanning with subsequent manual verification by an experienced medical professional. The results of analysis which include average heart rates, number of normal and types of abnormal beats during different periods of time, are submitted to a physician for final verification and conclusion.

Real-time systems include event-monitors, bedside monitors, stress-test systems and other devices for monitoring 1-2 critically important parameters and generating alarm or presenting the output information on a monitor. These systems perform an incomplete examination tracking the changes in heart rate and sometimes changes in the ST-segment. While this information is important for real-time control of a test or treatment, a number of important ECG changes, including changes in Q-, T-, or P-wave amplitude, QT-duration, are not exposed by this analysis.

It is known to provide portable ECG monitors that will sound an alarm or other signal to alert the user or an attendant of abnormal or unusual changes in the waveforms of the ECG signal. Such devices are, for example, disclosed in U.S. Pat. Nos. 4,193,393; 4,679,144; 5,033,475; 5,501,229 and 5,724,983. A system is also known, from U.S. Pat. No. 6,038,469, that includes at least one monitoring module for receiving ECG signals, a circuit for analyzing the signal, a plurality of parameters related to a patient's ischemic condition, and a network for exchanging data with a central unit, either by hard wire or telemetry. The monitor can be used in an ambulatory application in which the ECG signals are recorded and later sent to a central processing unit or units, which may be capable of sending information and data to the portable unit(s).

Shusterman et al. U.S. Pat. No. 5,967,995 has identified small cumulative changes in the series of cardiac inter-beat intervals using the Principal Component Analysis (PCA). This method accurately identified unstable dynamics of cardiac rhythm and predicted cardiac arrhythmias as early as several hours before the event when all known physiological indicators remained normal. The Shusterman et al. invention further extends the applications of PCA to the ECG signal.

Methods of artificial intelligence, also referred to as expert systems and neural networks, are well known and are in commercial use. Artificial intelligence is generally understood to mean the science and engineering of making intelligent machines, especially intelligent computer programs. Methods of artificial intelligence (expert systems and neural networks) are known in medicine as disclosed by Shusterman et al. in Building an application of Expert Systems For Differential Diagnostics of Cardiovascular Diseases, SAMS, 1994, Vol. 14, pp. 15-24, Yan et al. in The Internet-based Knowledge Acquisition and Management Method to Construct Large-scale Distributed Medical Expert Systems, Comput Methods Programs Biomed. 2004 April; 74(1): 1-10, and Baxt et al. in A neutral Network Aid for the Early Diagnosis of Cardiac Ischemia in Patients Presenting to the Emergency Department with Chest Pain, Annuals of Emergency Medicine, December 2002 40:06, among other publications.

SUMMARY OF THE INVENTION

This invention provides a portable and easy-to-use system for structured and complete analysis and representation of electrocardiogram and its serial changes quantitatively for medical professionals and qualitatively for a lay patient who does not have any medical background. Structuring of the analysis is achieved by constructing the at least two, and preferably three, information scales that represent the most significant parameters at different level of detail. In addition to the ECG, the multi-scale analysis and representation can be applied to other physiological data that include but are not limited to blood pressure, cardiac output, vascular activity, temperature, respiration, cardiac, abdominal, or breathing sounds, blood flow, hormonal concentration, enzyme and protein levels, genetic, proteomic, and molecular data, neural activity, electroencephalographic activity, and other electrical, mechanic, sonic, biochemical, and biophysical processes in the human body. This multi-scale analysis and representation can also be applied to other information related to human life, including demographic (age, gender), environmental (pollution, job conditions), and psychological data. The values of the data obtained from individual patients can be compared with the average values obtained in a group or a population of patients to facilitate analysis of individual data and to determine the values that characterize groups of patients with similar characteristics and/or similar disorders.

A preferred embodiment of this invention further includes implementation of the multi-scale analysis. Specifically, this invention provides for the implementation of the multi-scale analysis on a distributed network of personal devices (which may include devices for registration and processing of electrocardiogram, electroencephalogram, blood pressure, cardiac output, temperature, respiration, vascular tone, blood glucose, and other biochemical, biophysical, biomechanical, hormonal, molecular, and genetic data) and centralized computers with a bi-directional communication between them. This distributed network allows: 1) uninterrupted data acquisition (continuous or discrete) anytime, anywhere, 2) fast transmission of the acquired information to the other computers on the network for processing and comparison with previously acquired serial data (including individual baseline data), 3) fast and accurate processing, analysis, and accurate detection of serial changes, 4) transmitting the results back to personal devices (held by the individuals and medical personnel) to inform them and adjust the monitoring thresholds.

On the network, the data and its processing may be distributed among the devices and computers according to the computational resources, time period of data acquisition, type(s) of a medical test(s), geographical location, professional and living environment. For example, one distributed personal network of devices and computers could be setup at home, a second network could be setup at a work place, a third network could be setup in a hospital, and a fourth one could be setup in a transportation system (such as a train or an airplane), so that all four networks are connected to each other and can exchange the information instantly. The personal devices may include devices for acquisition and analysis of electrocardiogram, electroencephalogram, electromyogram, blood pressure, impedance, vascular resistance, cardiac output, biochemical, genetic, proteomic, molecular, and other types of health and environmental data.

The advantages of the distributed processing include: 1) a higher computational power and speed of distributed parallel processing, which allow efficient implementation of such computationally expensive methods of artificial intelligence as neural networks, expert systems, and hybrid artificial intelligence systems, and other mathematical and statistical tools, and 2) fast exchange of information among the devices on the network as well as between different networks.

Low, intermediate and high-resolution scales are defined according to the corresponding software and hardware resources. A low-resolution (Scale I) represents a small number of the most important primary elements such as intervals between the heart beats, duration of PQ, QRS, and QT-intervals, amplitudes of P-, Q-, R-, S-, and T-waves. This real-time analysis is implemented in a portable device that requires minimum computational resources. The set of primary elements and their search criteria are adjusted for each ECG utilizing computational resources of intermediate or high-resolution levels. At the intermediate-resolution (Scale II), serial changes in each of the said elements are determined using a mathematical decomposition into series of orthogonal basis functions and their coefficients. This scale is implemented using a specialized processor, a personal digital assistant (PDA), or a computer organizer. These devices could be used both by individuals and medical personnel, which allows fast and efficient transfer of information from individuals to medical personnel and back from medical personnel to the individuals. At the high-resolution (Scale III), serial changes in all elements of the ECG and their combinations are extracted using orthogonal mathematical decomposition to provide complete information about the dynamics of the signal. This scale is implemented using a powerful processor, a network of computers or the Internet.

Scale I may be implemented in a portable, pocket-size device, in which the signal is decomposed into a plurality of primary elements and parameters such as intervals between the heart beats, type of a cardiac complex, amplitudes and duration of P-, QRS, T-, and U-wave, QT-interval, amplitude of ST-segment. Scale I of the system provides the means for real-time electrocardiographic analysis by comparing the primary elements of ECG with reference values such as and including baseline values (individual thresholds) using the minimum computational resources. The reference or baseline values are programmed into the device based on normal values for the primary elements for the patient. Scale I includes means for adjustment of individual thresholds and criteria for rejection of noisy data. A detector of noise and error rejects the noisy data if the primary elements exceed physiologic range. Alternatively, modification of the primary elements and adjustment of their search criteria can be performed automatically at the higher-resolution Scale II or Scale III. In this case, the Scale I analysis is implemented using a programmable microprocessor that can be re-programmed at the higher-resolution scales to account for the individual characteristics of the ECG pattern and monitoring goals. Specific sets of primary elements can be used for patients with different cardiovascular abnormalities.

Scale I can be used in two modes: static mode and dynamic mode. The static mode is used for one-time ECG examination in which the newly acquired primary elements are compared with the default reference or baseline values. The dynamic mode is used for comparison of the newly acquired primary elements and waveforms with the primary elements and waveforms that were previously acquired from the same person. The shapes of QRS, T, and P-waves are compared using cross-correlation function. A small magnitude of the difference between the two measurements permits classifying them as substantially similar and keeping only one measurement in the memory.

Scale I provides sufficient information for standard, one-time, clinical ECG examination. The most significant primary elements may be represented as a color, symbol, or other easy-to-read encoding of indicators that make the results useful and understandable for a lay person and a medical professional. Each signal-indicator corresponds to a single primary element. In the static mode, the values of the indicators are preferably color-coded for a lay person into normal, moderately or severely abnormal. This representation constitutes a static screen. Alternatively, the indicators may be symbol-coded, N for normal and A for abnormal reading; they may vibrate or produce a sound output for people with vision or hearing impairments. For a medical professional, the indicators provide exact, quantitative values of the primary elements. In the dynamic mode, the indicators are preferably symbol (or color)-coded into C for changed or U for unchanged. This representation constitutes a dynamic screen.

Intermediate-resolution Scale II allows viewing the ECG with automatically determined primary elements on a display and interactive editing of the set of primary elements and their search criteria. The editing can be performed by a user or a medical professional to modify the set of characteristic points or to adjust their search criteria, and can be performed either manually or automatically by the software. The individually adjusted search criteria can then be used to re-program the Scale I analysis as described earlier.

Scale II allows accurate comparison of serial ECGs and detection of small serial changes that may be unexposed by visual inspection of the signals. This scale requires higher computational resources than Scale I and can be implemented in a specialized processor, computer organizer, a personal digital assistant (PDA), a cell phone, a smart phone (a combination of a cell phone and a PDA), or a personal computer. These computational resources also allow manual entering text information about the patient into the database and specific instructions regarding adjustment of time windows, threshold values, and other variables. To perform the Scale II analysis, the primary elements from serial ECGs are stored into a database to construct the time series for each primary element. The series is decomposed into a few most significant basis functions and coefficients using Principal Component Analysis (PCA) or any other orthogonal set of basis functions. The newly acquired values of the primary elements are compared with the series of the previously obtained values. Furthermore, the changes in the series of PCA coefficients are analyzed to detect small cumulative changes in the dynamics of the series that indicate instability in the cardiac electrical activity.

High-resolution Scale III is used to analyze individual and combined changes in the primary elements; at this scale, the number of the primary variables is increased to include the entire waveform of the cardiac complexes. This allows the most sensitive and accurate detection of the small changes in the individual electrocardiographic pattern. The same PCA approach is used at this scale to expose small serial changes in the ECG recordings. Scale III requires higher computational resources compared to Scale I and Scale II; it may be implemented in a powerful processing unit such as a personal or specialized computer or a distributed network of computers or the Internet.

Systems and analysis units made in accordance with this invention preferably include software and devices for exchanging information and data between the low resolution analysis modules or units and higher resolution modules or units in order to improve the functionality of the analysis. Such improved functionality can be in accuracy, efficiency, speed, usefulness or meaningfulness of the analysis. The exchange of data can also include instructions from a higher level analysis unit to a lower level analysis unit to adjust the analysis or select different primary elements to be analyzed.

This invention can be used for one-time examinations by patients, medical professionals, paramedics and lay public, and for dynamic assessment of changes in cardiac electrical activity. The information can be transmitted to an external computer system or a network of computers. For a lay person, the system may also include a database explaining significance of the changes in each primary element and providing simple recommendations about the measures that has to be taken if the readings of the indicators become abnormal. These may include complete cessation of physical activity, contacting a medical professional, taking a medication, etc. More detailed recommendations might be provided for patients who have specific abnormalities or medications. These patients might require special monitoring or individual adjustment of their primary elements. For example, specific monitoring the duration of QT-interval is important in patients taking antiarrhythmic drugs that prolong QT-interval.

The system can be used as
  first-aid ECG analyzer for emergency units, paramedics, and medical personnel;
  ECG analyzer for a routine medical examination;
  a personal one-time or serial ECG analyzer with storage of individual electrocardiographic historic data, adaptive adjustment of individual thresholds and assessment of changes in individual ECG pattern;
  a one-time or serial ECG analyzer for a group of people, a family or a patient group, with storage of individual electrocardiographic historic data for each person, adjustment of individual thresholds and assessment of changes in individual ECG patterns;
  event-monitoring device including patient-detected events, changes in heart rate or ST-segment;
  arrhythmia, bed-side, stress-test monitoring;
  pacemaker and other implantable device checking;
  evaluation of the treatment efficacy, side effects and progression of the disease.

The multi-scale analysis and representation can be applied for
  improved detection of changes during one-time examination,
  for assessment of short term and long term dynamics, which include fitness level, disease progression, treatment and side effects control,
  physical examination, early detection of subtle changes, and timely initiation or correction of therapy,
  early prediction and prevention of physiological disorders and abnormalities,
  examination of patients with implanted cardiac devices, including pacemakers and cardioverter-defibrillators.

Accordingly, an object of this invention is to provide a system for analyzing ECG and/or other physiological data at least at two levels of detail or resolution. Both levels of resolution are presented in simple representation that can be understood by lay persons, as well as medical professionals.

A further object of this invention is to provide an ECG analyzing system that includes a monitoring device for receiving and analyzing ECG signals and which includes means for communicating with an external computer to which the ECG signals can be forwarded for more complex analysis. The monitoring device can be reprogrammed by the external computer to select the primary elements of the ECG signals that are unstable or abnormal. The low level analysis performed by the monitoring device is thus focused on the critical primary elements for that patient.

The above and other objects and advantages of this invention will be more fully understood and appreciated by reference or baseline to the following description and the drawings.

BRIEF DESCRIPTION OF THE DRAWINGS

A full understanding of the invention can be gained from the following description of the preferred embodiments when read in conjunction with the accompanying drawings in which:

FIG. 4 shows the set of output indicators that represent the results of ECG analysis at Scale I both qualitatively and quantitatively in a dynamic mode ("U" represents unchanged value and "C" represents a changed value of a characteristic parameter compared to a previous recording).

FIG. 10 shows the readings from the indicators at Scale I in the dynamic mode for the abnormal ECG in FIG. 9.

DESCRIPTION OF THE PREFERRED EMBODIMENTS

Figure 1:
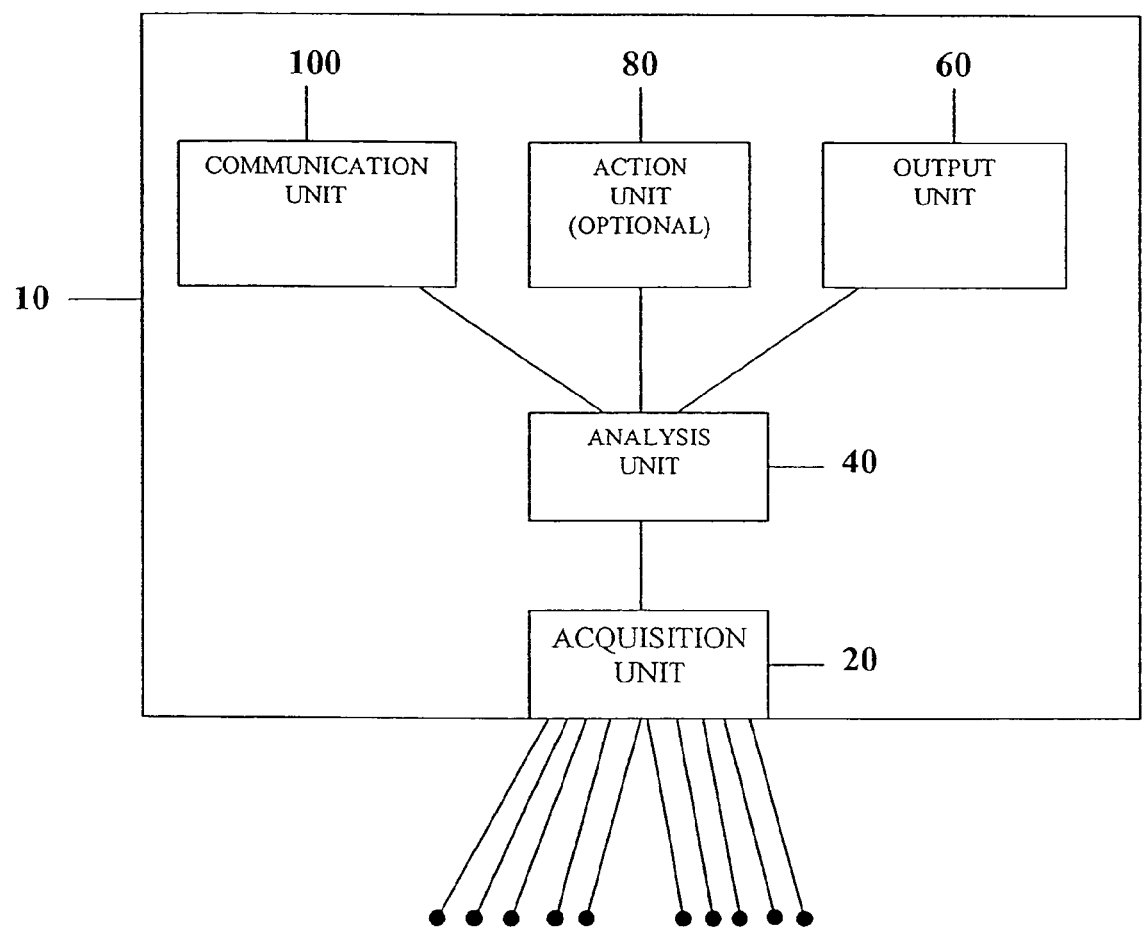
FIG. 1 is a block diagram of the medical device of the preferred embodiment of this invention.
Figures 2, 3:
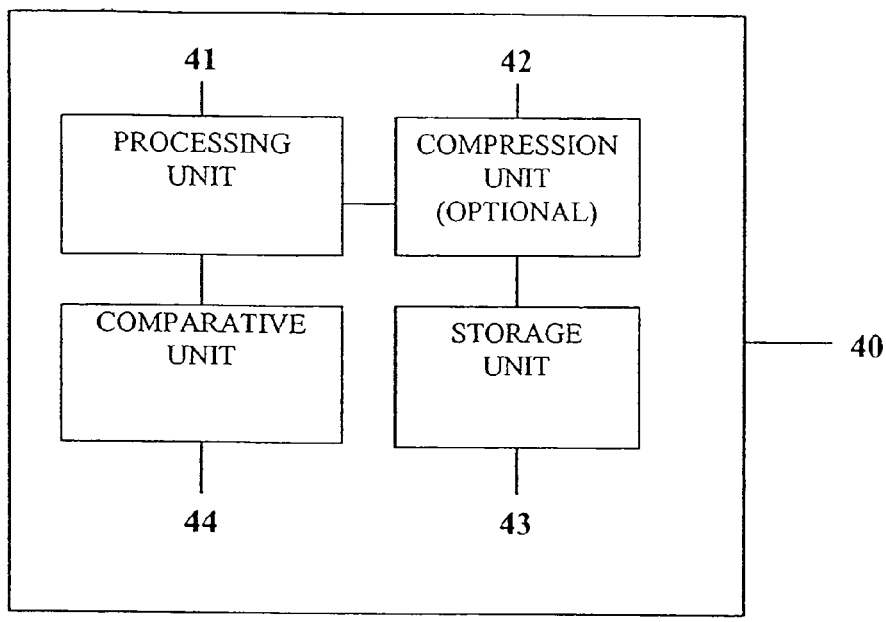
FIG. 2 is a block diagram of the analysis unit from FIG. 1.
FIG. 3 shows the set of indicators that represent the results of ECG analysis at Scale I both qualitatively and quantitatively in a static mode ("N" denotes normal value and "A" denotes an abnormal value of a characteristic parameter).

FIG. 1 is a block-diagram of a preferred embodiment of a medical device 10 of this invention. The device consists of an acquisition unit 20 that may have several electrodes 25 for attachment to a patient, not shown, to receive electrocardiographic and/or other physiological data, an analysis unit 40, an optional output unit 60, an action unit 80 and a communication unit 100. Standard ECG recorders having acquisition units and storage units are available from several companies such as Hewlett-Packard (Model 1700A) and GE Marquette Medical systems (Mac 500). Portable ECG monitors that record and store segments of ECG are available from Integrated Medical Devices (Model 1200). Alternatively, the ECG data could be acquired by an implanted cardioverter-defibrillator or a pacemaker, such as Prism™ or Contak™ devices produced by Guidant Corp. (St. Paul, Minn.) or Jewel™ or Marquis™ instruments manufactured by Medtronic Inc. (Minneapolis, Minn.). The acquisition part may receive ECG data from a recorded data source for analysis, but preferably receives the data real-time, on-line through the electrodes 25 that are connected to a patient. As used herein, patient means an animal, and most likely a human. The medical device further includes an analysis unit or module 40 which, in turn, consists of processing, compression, storage, and comparison units (FIG. 2). The processing unit 41 can be a typical computer or personal computer of the type available from many vendors such as IBM and Hewlett-Packard. The processing unit 41 is programmed to detect a plurality of characteristic points such as the onset, peak and offset of P-, Q-, R-, S-, T-, U-waves, and computes the characteristic parameters or primary elements which include amplitudes of the said waves and ST-segment, duration of PQ-, QRS-, and QT-intervals. The processing unit 41 has a programmable microprocessor that can be programmed to modify or change the set of primary elements or to adjust their search criteria. This allows individual adjustment of the characteristic points which, in turn, increases the accuracy of detection of the primary elements. For instance, in signals with biphasic T-wave, two T-peaks should be detected, whereas monophasic T-wave requires detection of a single T-peak. Furthermore, the criteria for determining the offset of biphasic T-wave are different from the criteria for the offset of monophasic T-wave. Individual adjustment of the primary elements and their search criteria increases the accuracy of the detection of characteristic points in different ECG patterns. Still another possibility is analysis of combined changes in some primary elements or disabling analysis of the other elements. For example, in patients with possible electrolyte abnormalities, the amplitudes of the T-wave and U-wave may be combined into a single index which will be convenient for monitoring. Furthermore, the set of monitored primary elements can be modified according to the specifics of cardiovascular abnormality. For example, in patients with coronary artery disease, the amplitude and the slope of the ST-segment should be monitored continuously.

Compression unit 42 compresses the ECG waveform into a few weighted basis vectors and their coefficients using principal component analysis, wavelet decomposition, or other orthogonal mathematical transformation. Storage unit 43 stores the compressed waveforms and the computed primary elements into memory. Comparative unit 44 compares the newly acquired waveforms and newly computed primary elements with the waveforms and primary elements previously stored in the storage unit 43. The analysis unit 40 has means for adjusting the thresholds for each indicator, whereas the default values correspond to normal ECG. An output unit 60 includes a screen or a set of indicators for displaying the ECG waveforms and the computed primary elements in comparison with the previously stored primary elements or in comparison with the default reference or baseline values. The results of comparison can be represented both qualitatively and quantitatively in the dynamic and static modes. In the static mode, the quantitative representation includes exact values of the primary elements and the type of the cardiac complexes, whereas the qualitative representation includes indication of each parameter as being normal (N) or abnormal (A) as shown in FIG. 3. Abnormal readings may be further classified into moderately abnormal and severely abnormal. To make the indicators understandable to a lay person, the degree of abnormality may be color-coded: green color corresponds to a normal value, yellow corresponds to a moderate abnormality, and red corresponds to a severe abnormality. In the dynamic mode, the quantitative representation shows the differences between the newly acquired and stored primary elements and waveforms, whereas the qualitative representation includes indication of each parameter as being changed (C) or unchanged (U) as shown in FIG. 4. The output unit 60 may alternatively or additionally feed an output data to an action unit 80 for sounding an alarm, generating a vibration, or taking appropriate measures, such as applying the drugs or adjusting the therapy mode. Communication unit 100 transmits the information between the device 10 and external higher-level processing device 150. The communication unit 100 may be a modem or a wireless transmitter/receiver. The wireless communication can be implemented using Bluetooth wireless technology (from The Bluetooth Special Interest Group (SIG) trade association) or other radiofrequency transmission technology, infrared, magnetic or nuclear type of a wireless transmission. The communication can be also implemented using a local area network, a Wi-Fi network, a cell phone transmission technology, a personal digital assistant (PDA) with wireless communication module (for example bluetooth communication), a smart phone (a combination of a cell phone and a PDA) a GPS (global positioning system), GSM World™ from GSM Association (wideband mobile multimedia), GPRS™ wireless from General Packet Radio Service, satellite, or other wireless communication systems. Electrocardiographic signals and recorded values of primary elements and indexes are transmitted from the device 10 to higher level devices for more detailed processing and storage. The higher-level device 110 preferably transmits back to device 10 a set of primary elements and their search criteria to be used in device 10.

Figure 5:
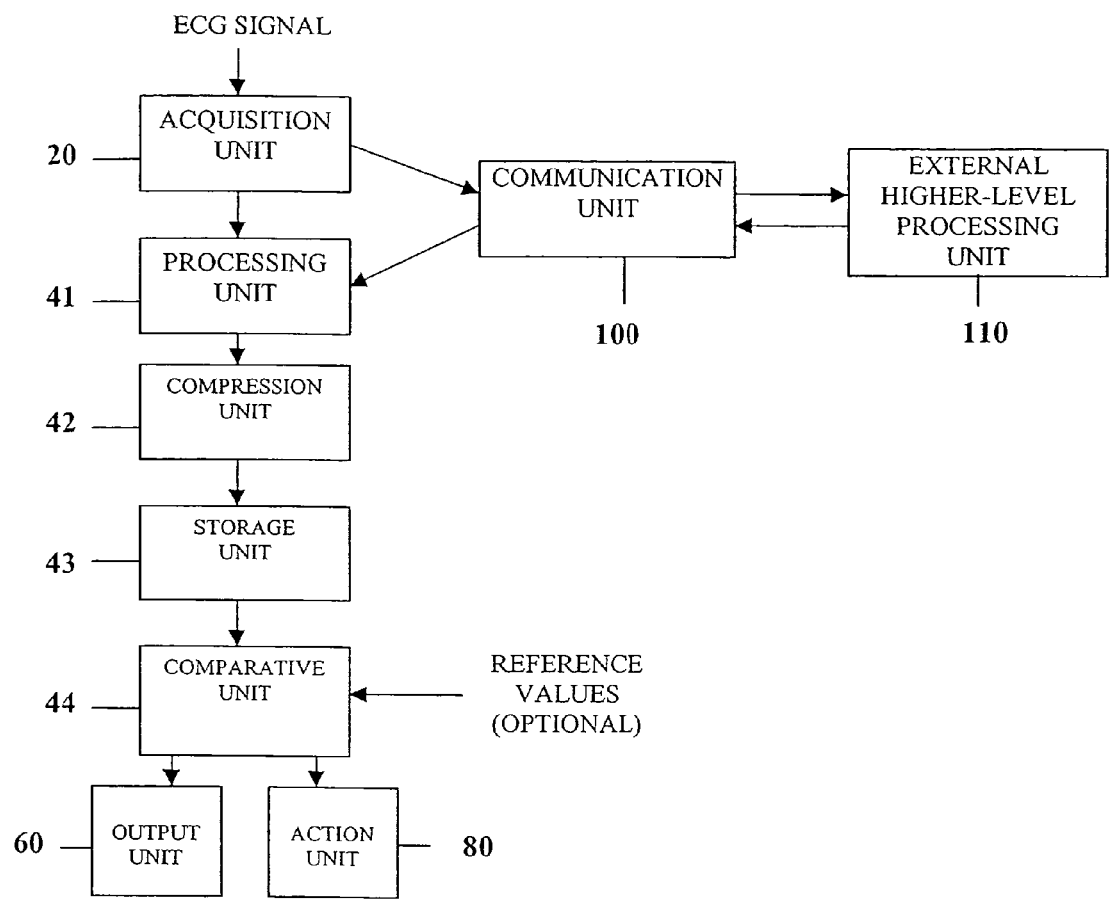
FIG. 5 is a flowchart of operation of the preferred embodiment.

FIG. 5 is a flow-chart of operation of this medical device.

Figure 6:
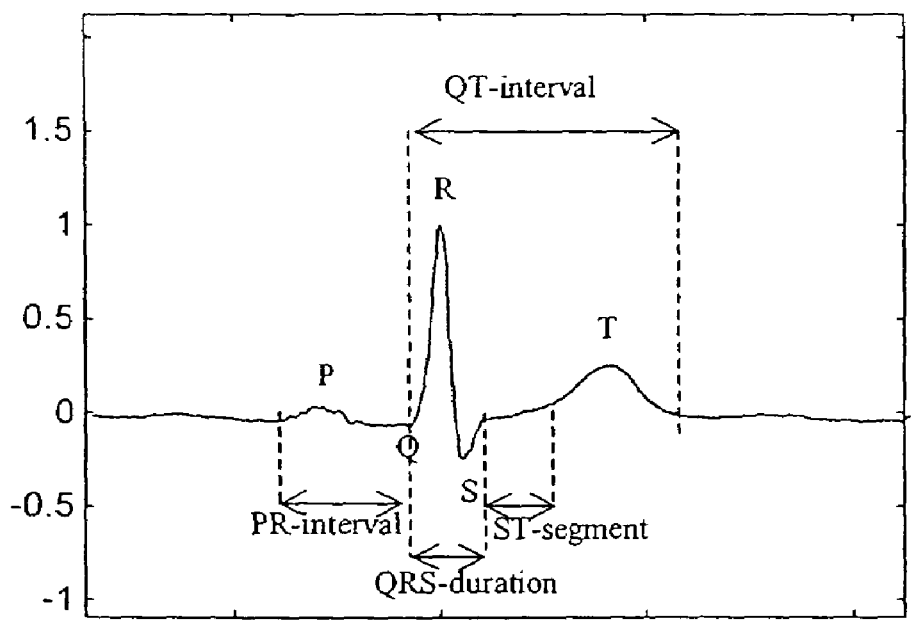
FIG. 6 is a graph of a representative electrocardiogram from a normal subject and its segmentation into a plurality of characteristic points and segments.

FIG. 6 shows a representative ECG obtained from a normal subject and position of the characteristic points in the signal.

To achieve the optimal sensitivity in the detection of hidden or small ECG changes, a pattern recognition approach is used that extracts the basis functions from the statistics of the signal itself and gives the least error representation of the signal. Specifically, a principal component analysis (PCA) is applied which requires a minimum number of basis functions to obtain a fixed reconstruction error compared to other orthogonal expansions.

PCA is an orthogonal transformation that employs a weighted combination of several basis functions to represent a signal. The basis functions are fixed, whereas PCA-coefficients vary as a function of time. The choice of PCA for detection and characterization of the changes in ECG-signal was related to the following properties of the transform:

minimization of the mean square error within a finite number of basis functions guarantees that no other expansion will give a lower approximation error (with respect to the mean square error).

clustering transformational properties with minimization of the entropy in terms of the average squared coefficients used in the expansion.

In contrast to the methods that use fixed-form basis functions (for example, Fourier representation), basis functions in PCA are derived from the statistics of the signal. Therefore, PCA with the same number of basis functions provides a smaller residual error than other expansions.

Assume that the pattern contains M vectors $x_i$ i=1, 2, ..., M, and the length of each vector is equal to N points. To obtain the PCA coefficients, the matrix $C_x$ must be obtained using the average of the covariance matrices of x vectors. The matrix $C_x$ is defined as $$C_x = E\{(x-m_x)(x-m_x)^T\} \quad (1)$$

where $$m_x = E\{x\} \quad (2)$$

is the mean vector, and E corresponds to the expected value. Assume that the pattern of the time series has M unit-length vectors $x_i$, i=1, 2, ..., M, and the length of each vector is equal to N points, to generate a matrix $C_x$ from the outer products of vectors x. A matrix $C_x$ of M vectors $x_i$ can be calculated as $$C_x \cong \frac{1}{M} \sum_{i=1}^{M} \{(x_i - m_x)(x_i - m_x)^T\}, \quad (3)$$

where i=1, 2, ... M, and $$m_x \cong \frac{1}{M} \sum_{i=1}^{M} x_i \quad (4)$$

From the matrix $C_x$ one can obtain eigenvectors $\psi_i$, i=1, 2, ..., N and corresponding eigenvalues $\lambda_i$, i=1, 2, ..., N. Let A be the transformation matrix whose rows are the eigenvectors of $C_x$. First eigenvector corresponds to the first eigenvalue, second one corresponds to the second eigenvalue and so on. Eigenvalues are arranged in decreasing order so that $\lambda_1 \geq \lambda_2 \geq ... \geq \lambda_N$. Then, PCA consists of a multiplication of the transformation matrix A by vector $(x-m_x)$:

$$y = A(x - m_x) \quad (5)$$

where y is a PCA coefficient vector. If matrix A is formed by K eigenvectors that correspond to the largest eigenvalues, y is a K×1 vector. Then, the first K coefficients contain almost entire information about the signal allowing substantial reduction in the number of analyzed coefficients and thus compression of the data. In this application, PCA is applied to the time series of each primary element, that is the intervals between the cardiac beats, duration of PQ, QRS, and QT-intervals, amplitudes of P-, Q-, R-, S-, and T-waves. For instance, to determine the characteristic pattern of the series of QT-intervals from the serial ECGs, assume that the pattern consists of M unit-length vectors $x_i$. Therefore, the series is divided into M constant-length time windows to obtain vectors $x_i$. Alternatively, the unit-length vectors $x_i$ may be comprised of a combination of all or some primary elements to determine a typical combinatorial pattern of the primary elements. Still another possibility is an extension of the concept of the unit-length vectors $x_i$ into two dimensions to represent both the combined pattern of all primary elements (in the first dimension) and the serial changes of each primary element (in the second dimension). Then PCA analysis is performed as described above.

Applications of the Principal Component Analysis at Scale II and Scale III of the System The analysis described hereafter could be used as a stand-alone tool or a part of an integrated processing and analytical system, such as an artificial intelligence system, which includes neural networks and expert systems. The analysis could be performed on a single computer or a distributed computer network, possibly, with parallel processing. In previous works, PCA was applied for detection and classification of cardiac waveforms (QRS-complexes and ST-segments) in ECG. The optimal basis functions for QRS or ST waveforms were obtained from large training sets. PCA coefficients were used to compare individual waveforms with the set of templates and to assign the waveform to one of the classes.

Instead of applying PCA to the signal as in the previous art studies, this invention preferably applies PCA to the time series of primary elements that are extracted from the ECG-signal. This modification provides the following advantages. First, this provides an objective and accurate estimation of the serial changes in the ECG-signals and reveals small or hidden abnormalities that cannot be exposed by the previously used techniques. Second, this allows dramatic compression of the data. Third, this analysis reveals independent changes in each primary element when simultaneous changes occur in several elements. The prior art analysis of the original ECG signal might not show any changes because of the cancellation effects between the elements undergoing changes in opposite directions.

Because the time series of primary elements is nonstationary and highly variable among subjects and in the same subject over different periods of time, typical waveforms or templates of this series cannot be determined. Therefore, temporal, adaptive changes in PCA coefficients are used to detect and characterize the changes in this series. Pronounced and complex changes in the series of primary elements are identified by the simultaneous changes in several PCA coefficients. Since the basis functions in this expansion are orthogonal, simultaneous changes in several coefficients represent complex disturbances in linearly independent components of the signal. These combined changes in PCA coefficients reveal serious instabilities in the cardiac function as shown in the following examples.

The signal is separated into consecutive windows, and an array of vectors is obtained from the series. A covariance matrix is formed by the formula (3), where M is the number of vectors, $x_i$ is $i^{th}$ vector, and $m_x$ is calculated as in formula (4). Basis functions or eigenvectors are obtained from this matrix. Since only one covariance N×N matrix (N is the window length) is generated from the signal, all eigenvectors are fixed.

In addition to the changes in the PCA-coefficients, changes in the basis vectors (eigenvectors) can be used to evaluate the changes in ECG and its variables and/or other physiological data at different scales. Furthermore, if the set of eigenvectors is fixed, changes in their energy (eigenvalues) can also be used for estimation of the changes in the signal and the parameters derived from the signal at different resolutions. In particular, at the low resolution scale, the analysis could be limited to the estimation of changes in the spectral characteristics of a few, most significant eigenvectors and the corresponding eigenvalues. At the higher-resolution scales, the analysis may include a greater number of studied eigenvectors and eigenvalues, and estimation of their combined changes.

EXAMPLE I

The following example illustrates the sequence of ECG analysis at the system's Scales I, II and III. Serial ECG recordings from a patient A who had a structural heart disease and dynamic changes in the electrocardiogram were processed at each Scale with a different degree of detail. Scale I revealed the changes in a small number of important, primary elements using minimum computational resources. Scale II exposed changes in the primary elements that occurred in serial recordings over time. Scale III provided complete description of the serial ECG changes using a complete set of primary elements and their combinations.

Figure 7:
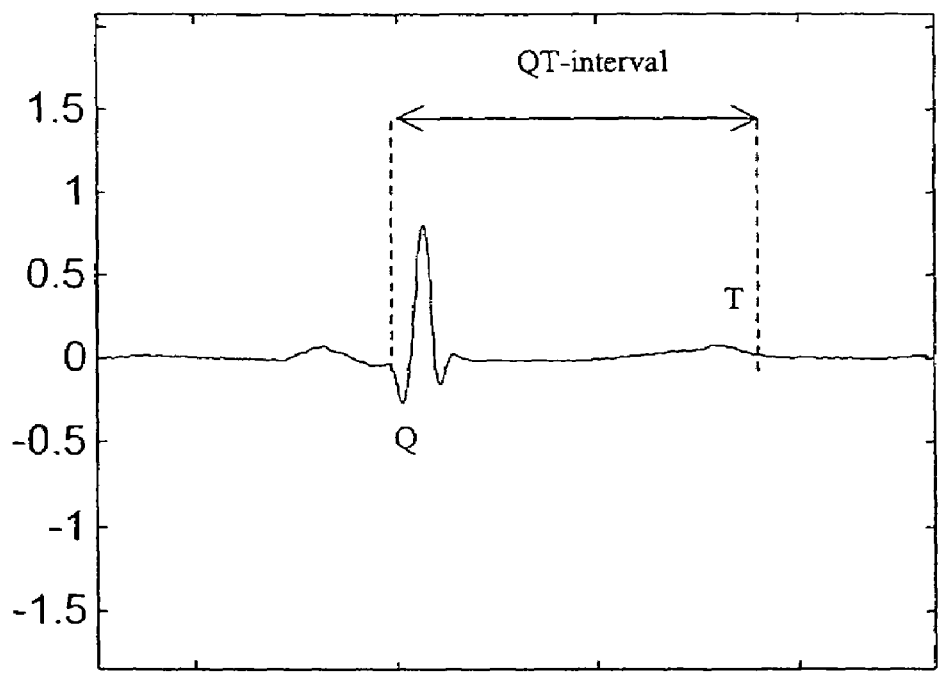
FIG. 7 is a graph of a representative electrocardiogram from a patient with a cardiac disease, large Q-wave, and prolonged QT-interval (0.5 sec) compared to the normal ECG shown in FIG. 6.

System initialization. When the system is used for the first time, initialization is required for verification and individual adjustment of the analysis criteria including identification of the primary elements and their search criteria. System initialization is performed using the hardware and software resources of the intermediate resolution Scale II and high resolution Scale III. In the initialization mode, the Scale I device transmits ECG to the higher Scale of the system via a direct or a wireless (telemetry or infrared) link. The ECG and the position of primary elements and their characteristic points (onset, peak, and offset) are visualized on a display, for example LCD display, as shown in FIG. 6. The position of characteristic points can be verified and manually edited by a user, a lay person or a medical professional. A simple manual or a software tutoring program of the typical ECG patterns, the primary elements and their characteristic points is provided for a lay person. FIG. 7 shows an ECG with a long QT-interval (0.5 sec) and a low-amplitude T-wave compared to the normal ECG shown in FIG. 6. The offset of this low-amplitude T-wave is difficult to detect automatically and a manual verification and correction are desired to ensure the accuracy. A user may also modify the set of monitored primary elements to account for a specific cardiovascular abnormality. Some of the elements may be combined into a single monitoring index, for example, a combined integral of T and U peaks can be useful for patients with possible electrolyte abnormalities.

After finishing manual verification and editing, the system automatically adjusts the search criteria for each characteristic point which include the time window, the amplitude, integral and derivative thresholds. The individually adjusted program is generated for a particular person and is automatically sent to re-program the processing sub-unit of Scale I. After the initialization, the Scale I device can work in autonomous regime without permanent connection to the higher-level Scales.

Re-initialization and serial adjustment can be performed to modify the set of primary elements and indexes and their search criteria. In addition to the procedure that was described in the system initialization, the results of the Scale II analysis can be used for serial adjustment. In particular, the primary elements and indexes whose time series and PCA coefficients demonstrate unstable behavior can be identified and included into the Scale I analysis.

Figures 8, 9:
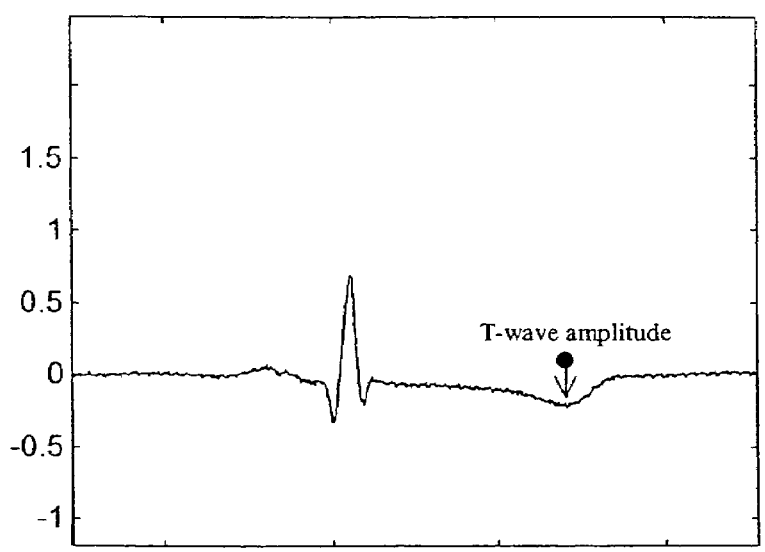
FIG. 8 shows the readings from the output indicators at Scale I in the static mode for the abnormal ECG in FIG. 6 (N denotes normal value, A denotes abnormal value of a characteristic parameter compared to default values).
FIG. 9 is a graph of ECG obtained from the same patient as in FIG. 8 several hours later. The amplitude of T-wave decreased by 0.3 mV compared to the previous recording shown in FIG. 7.

Scale I. FIG. 7 is a graph of a representative electrocardiogram which has large Q-wave, and prolonged QT-interval. These abnormalities have been detected by the method of the present invention at the Scale I and represented qualitatively as abnormal findings and quantitatively as the exact magnitude of changes compared to the default values as shown in FIG. 8 which are readings of output indicators at Scale I for abnormal (A) and normal (N) ECG in the static mode. FIG. 9 is a graph of ECG obtained from the same patient several hours later. The amplitude of T-wave decreased by 0.3 mV compared to the previous recording shown in FIG. 8. The amplitude of T-wave decreased by 0.3 mV compared to the previous recording shown in FIG. 7. FIG. 9 shows the readings from the output indicators that represent the changes (C) in this ECG compared to the previous one.

Figure 11:
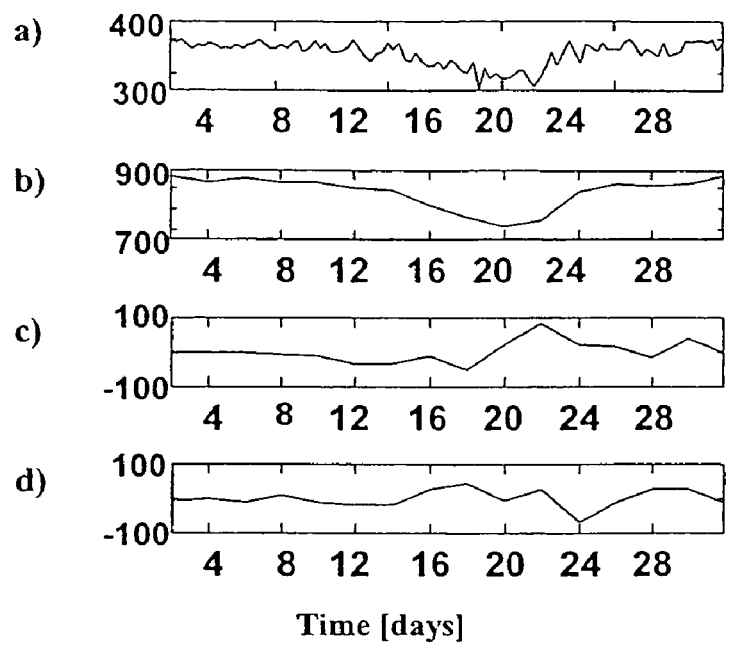
FIG. 11 shows the time series of QT-intervals (panel A) and its first three PCA-coefficients (panels B-D) in patient A during one month.
Figure 12:
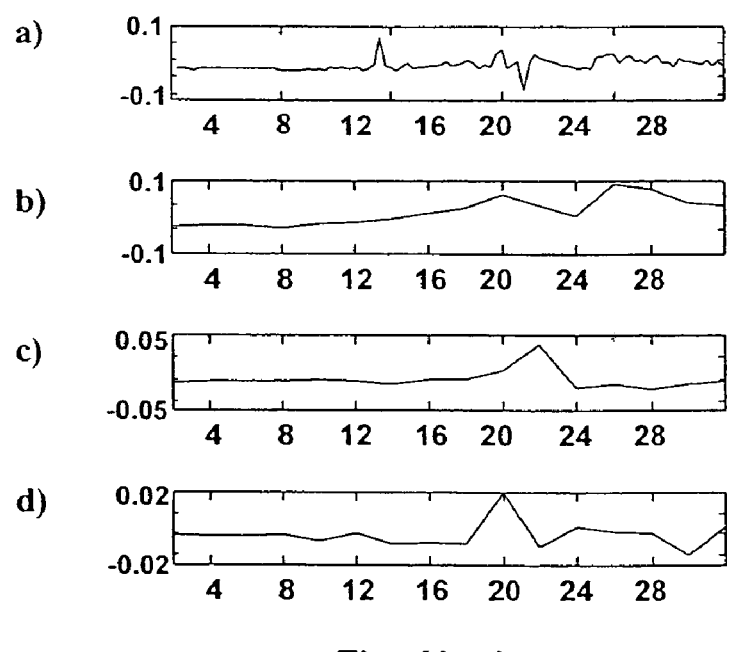
FIG. 12 shows the time series of T-wave amplitudes (panel A) and its first three PCA-coefficients (panels B-D) in patient A during one month.

Scale II. Serial ECGs have been obtained from patient A. and processed by means of Scale II to expose the time course of the serial changes that occurred in the this patient over a period of 1 month. FIG. 11, panel a, represents the series of QT-intervals that were extracted from these recordings; panels b-d demonstrate the changes in the first three PCA-coefficients that were obtained from this signal. At the end of the last recording, the patient developed a life-threatening disorder of cardiac function. However, this method reveals instability in the cardiac function as early as 20 days before the event when all known physiological indicators remain normal. FIG. 12 demonstrates changes in the T-wave amplitude extracted from the same recordings (panel a) and the corresponding first three PCA-coefficients. The time series are complex and the changes cannot be easily described or analyzed by simple tools, therefore, the changes in the signal are analyzed in a compressed form using the series of the first three PCA-coefficients which contain the most significant information about the signal. The ECG was relatively stable during the first 10 days but then became unstable as reflected by variations in the PCA-coefficients. The patient suffered a life-threatening cardiac disorder at the end of the month. However, variations in the PCA-coefficients were observed long before the event, when all physiological indicators remained normal. Calculating the changes in the variance of the PCA coefficients provides an accurate estimation of the changes and stability of the series. Unlike linear estimators such as the mean and variance of the signal or nonlinear estimators such as fractal scaling exponent or correlation dimension, disturbances in the PCA coefficients are indicative of any changes in the pattern of the signal. Therefore, analysis of PCA coefficients reveals both linear and nonlinear changes in the signal.

Figure 13:
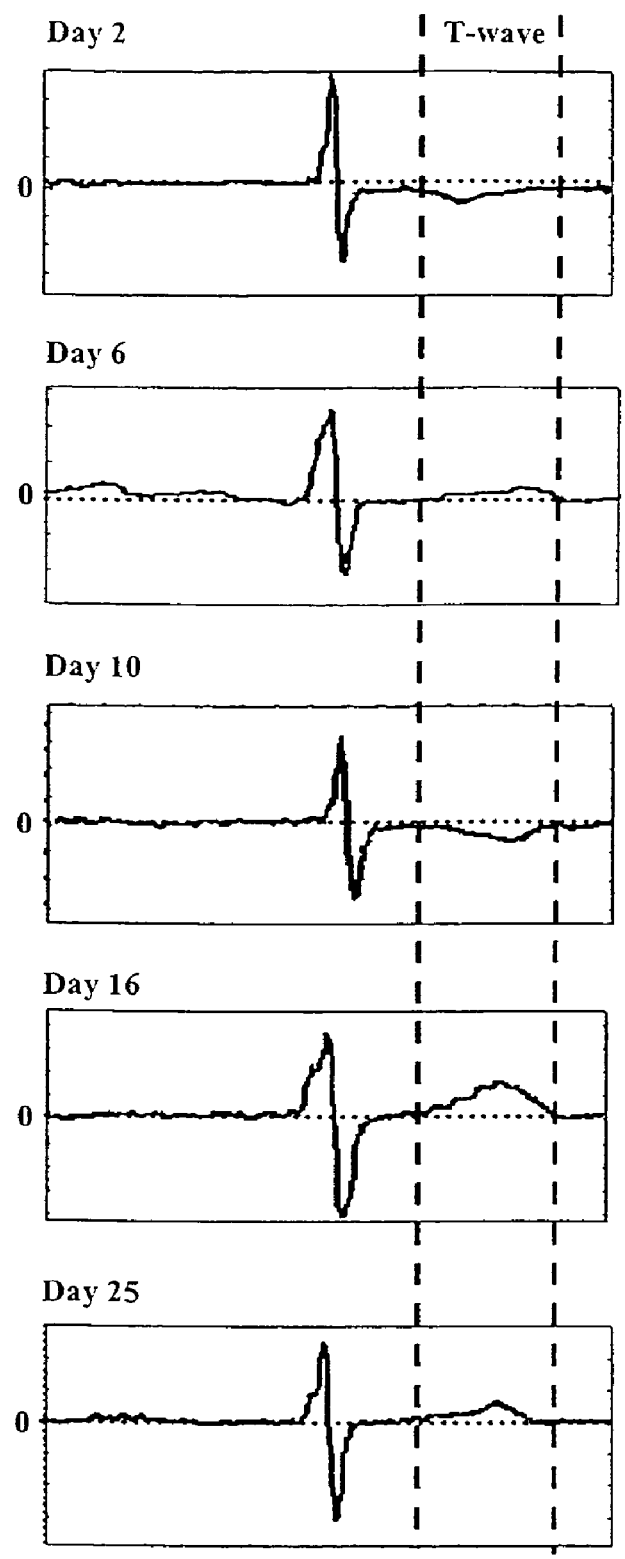
FIG. 13 shows serial ECG tracings of patient A during one month.

Scale III. The same ECGs that were analyzed at the Scales I and II, were further processed by means of Scale III to expose the entire dynamics of the ECG signal. FIG. 13 demonstrates the ECG waveforms that were obtained from serial ECG recordings in patient A. Since all the data points are included into the analysis, the changes in the shape and polarity of T-wave can be easily detected in the serial ECGs using visual inspection, PCA or other signal processing tools. The polarity of the T-waves are negative in days 2 and 10 recordings, and are positive in days 6, 16 and 25 recordings.

Figure 14:
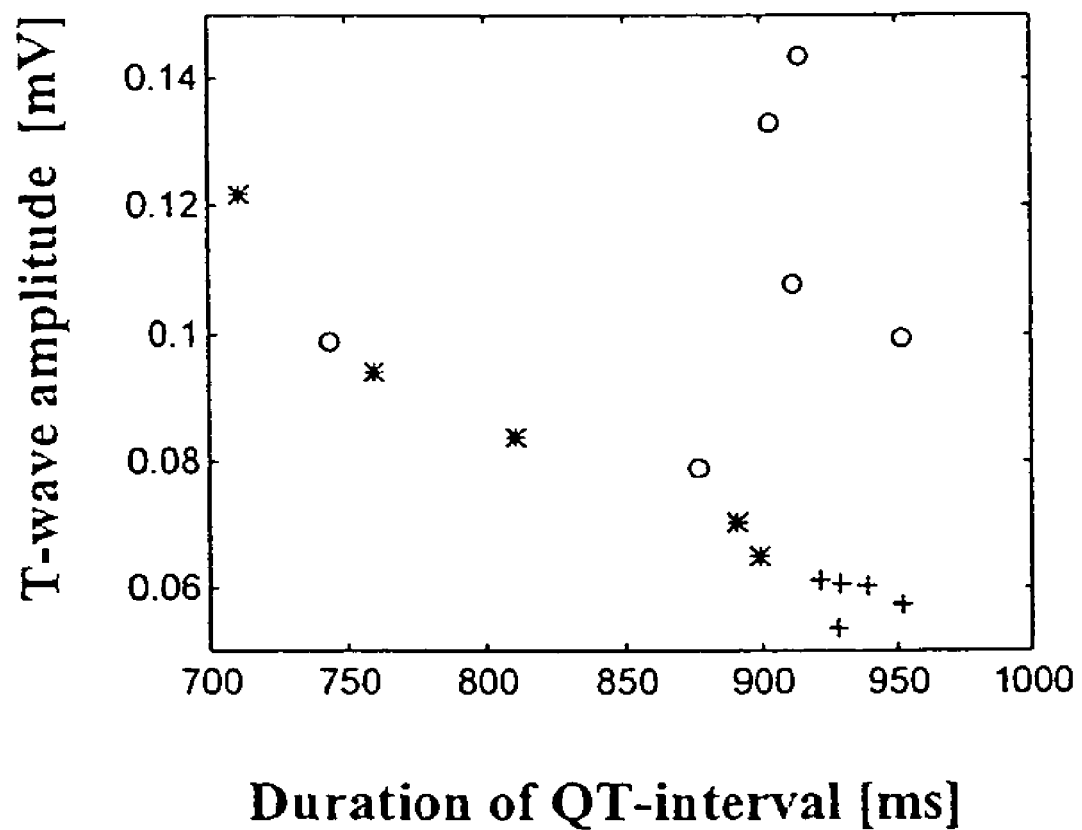
FIG. 14 is a plot of the first PCA-coefficient obtained from the series of QT-intervals versus the first PCA-coefficient obtained from the series of T-wave amplitudes in patient A.

FIG. 14 shows the changes in the PCA coefficients of these series in Scale III, dynamics of ECG in patient A in a space of the first, most significant PCA-coefficients. Y-axis represents the first PCA-coefficient that was obtained from T-wave amplitude. X-axis represents the first PCA-coefficient that was obtained from QT-interval. Each point corresponds to one-hour value. Values during 1-5 days are marked as pluses, values during 6-10 days are marked by stars, values during 11-16 days are marked by circles. Higher dispersion and change in the location of the points during 6-16 days compared to the first five days indicates instability of serial ECGs. A small cluster of data points in the lower right corner of the figure corresponds to the unchanged signals during the first 5 days of the recording. Then, the dispersion of the points increases and their location changes which reflects increased instability of the signals. Thus, the combined changes in the coefficients that were obtained from different primary elements revealed instability in the cardiac activity that preceded aggravation of the cardiac disease.

EXAMPLE II

This theoretical example has been selected to show how the present invention could be implemented using a distributed network of computers with parallel processing and how it can be efficiently integrated with such methods of artificial intelligence as neural networks and expert systems to process different types of serial information obtained from a patient with chronic congestive heart failure. Patients with chronic illnesses often have a number of chronically or intermittently abnormal indicators, whose dynamics are difficult to discern. A network of computers allows fast and accurate processing of the patient's information obtained using different diagnostic techniques (such as biochemical, electrocardiographic, nuclear magnetic resonance, stress-test, and other modalities).

In a hypothetical patient B. with chronic congestive heart failure (Class II) and a three-year-old myocardial infarction, the above-described high-resolution analysis of serial ECG recordings could reveal a subtle decreasing trend in the amplitude of the ST-segment. This trend could be revealed because the serial ECG recordings were processed at the high-resolution level using a radial basis function (RBF) neural network, which was previously trained on patient's B. electrocardiographic data. Because the neural network could learn the typical patient's B. ECG pattern, it could detect subtle changes in this pattern. The magnitude of the changes may be so small and the changes so gradual, that they might escape detection by the standard ECG processing techniques, which are manually applied by the physicians or used by the current commercial ECG scanning software. The computer server, where ECG recordings from this and other patients would be stored and analyzed, would be a part of a computer network that also includes servers for analysis of biochemical, stress-test, nuclear magnetic resonance, and other data. The servers would be organized into a hybrid artificial intelligence system, which combines a neural network and expert systems. In this system, the neural networks are used where the rules of analysis can be modeled by a multi-node network structure, in which each node is assigned the specific input and output rules and connections to other nodes. On the other hand, expert systems are used when the decision making process due to numerous uncertainties is better represented by informal (heuristic) rules.

The above-described decreasing ST-amplitude trend in the serial ECG recordings lead to an activation of an expert system's rule that initiates query of other computer servers on the network that contain biochemical, stress-test, and nuclear-magnetic resonance date for the same patient. After that, the server that contained biochemical data initiates neural network analysis of the patient's enzyme level concentration for the period of time, in which ECG changes occurred. A small increasing trend is detected in the cardiac myoglobin levels, and this biochemical and ECG information are transmitted wirelessly to the personal digital assistant of an attending physician with a suggestion of a slowly developing ischemic process. The timely notification allows the physician to initiate early anti-ischemic treatment and prevent potentially life-threatening complications of the disease.

EXAMPLE III

This theoretical example is provided to show implementation of the present invention on a specialized computer network, which could be setup for individuals working in the high-demand professional environments, such as airplane pilots.

During a late-spring commercial flight, a hypothetical 46-year-old pilot suddenly developed dizziness and shortness of breath. A Scale I ECG examination showed sinus tachycardia (fast heart rates) and increased amplitude of the P-wave. The Scale I analysis is performed using a portable ECG acquisition unit, which transmitted the information wirelessly (using a Bluetooth radiofrequency communication technology to an integrated airplane health network (implemented using Wi-Fi wireless technology). A second Scale-I-device (also connected to the network) is used to examine changes in blood pressure and detected moderate increase in diastolic pressure.

The airplane integrated health system, which includes a diagnostic expert system, queries wirelessly the home network computer server of the pilot (using GPS wireless communication technology) to obtain the health data for the previous month. The home network server, in turn, activates Scale III serial analysis of all available health data and detects subtle but gradually increasing instabilities in heart rate and P-wave amplitude during the previous 3 days aggravated by physical exercises. In the health data file, the system also identifies information regarding the pilot's history of allergic reactions during the spring vegetation periods. This information is transmitted back to the airplane expert system, which combines the information and suggested an allergic bronchial spasm. This information is transmitted wirelessly to the personal digital assistant of an attending physician, who from his home network system sends back a recommendation of anti-allergic medication, which eliminates the symptoms.

Note that the multi-scale distributed system could be configured to operate in several different modes. In the first mode, which is activated in the airplane, the portable ECG acquisition and Scale-I-analysis unit transmits the data wirelessly to the integrated airplane health network for higher-resolution analysis. In the second mode, which is activated in a car, the portable Scale-I-analysis unit communicates wirelessly with the car computer network using a bluetooth technology. In the third mode (which is activated at home), the portable ECG acquisition and Scale-I-analysis unit transmits the data wirelessly to the home integrated computer health network (organized using Wi-Fi communication). In the fourth configuration (which is usually activated outside home, on vacations, etc.), the portable ECG acquisition and Scale-I-analysis unit transmits the data wirelessly to the personal digital assistant (PDA) or a cell phone or a smart phone (a combination of a cell phone and a PDA) for Scale II analysis. If needed, this Scale-II-analysis unit then connects wirelessly (using a cell phone GSM communication technology) to a home health computer network. Alternatively, this fourth mode of operation (with a PDA or a cell phone for Scale II analysis) could be selected to operate at home, in a car, in the airplane, and in other settings.

EXAMPLE IV

This theoretical example is selected to show application of the present invention for tracking dynamics of health data in patients with implantable cardiac devices.

A hypothetical patient with an implantable cardioverter-defibrillator has developed subtle instabilities of cardiac rhythm and slowly rising average heart rate. These changes are detected by the implantable device, which transmits this information wirelessly to a home health network computer. The network computer performs serial analysis of the recordings at Scale III resolution. At the same time, the computer reaches a hospital network server and queries the recordings from the same patient during his recent hospitalization. Inclusion of these recordings into the Scale III analysis shows that a similar instability of heart rate was observed in this patient only prior to onset of life-threatening cardiac arrhythmia. Another personal device (also connected to the network) for tracking changes in blood pressure shows instability of blood pressure. An artificial intelligence system (which was integrated with the Scale III analysis) is automatically activated to interpret these findings. The system assesses the findings as clinically significant and forwards them wirelessly to a personal digital assistant of an attending physician, who decides to initiate preventive beta-blocking therapy. During the next six hours of monitoring, the Scale II and Scale III analysis shows stabilization of cardiac rhythm.

EXAMPLE V

This theoretical example describes potential benefits of the present invention in patients with congestive heart failure undergoing bi-ventricular resynchronization pacing therapy (using the implanted bi-ventricular pacing device, such as a Medtronic Insync Marquis III™ device).

A hypothetical patient with chronic congestive heart failure undergoing resynchronization pacing for 15 months has developed a gradual increase in the T-wave duration and changes in the T-wave morphology, indicative of slowly progressing repolarization heterogeneity. These changes are detected by the implanted device, which used individually tailored monitoring thresholds at the Scale I analysis. The thresholds were adjusted using the individual patient's reference values determined at the Scale III analysis (which was performed on a hospital health network). The changes in the T-wave detected by the implanted device are transmitted wirelessly to the hospital computer network for higher-resolution, in-depth processing. The Scale III analysis confirms that the magnitude of the changes exceeded 5 standard deviations never been observed in this patient previously. The information is transferred to the integrated artificial intelligence system for further interpretation. The system classifies the changes as clinically significant and forwarded them to the medical personnel. Considering these changes, a decision is made to hospitalize the patient for detailed examination and therapy adjustment.

In addition to the above-described orthogonal linear decomposition, other methods of non-orthogonal decomposition or independent component analysis, multidimensional scaling based on non-metric distances and mapping techniques can be used for multi-scale analysis. These include but are not limited to non-orthogonal linear mappings, nonlinear mappings and other projection methods that make use of such mathematical tools as the domain and range straightening, and re-scaling (change of variables), methods from the theories of singularities, bifurcations, catastrophes, and dynamical systems. In addition, other statistical estimators, such as a linear and nonlinear correlation, analysis of variance, cluster analysis, factor analysis, canonical analysis, regression and discriminant function analysis, and probabilistic methods, such as Bayesian probability, pattern recognition, and methods of artificial intelligence, including neural networks, fuzzy logic, and expert systems, as well as hybrid (combined) artificial intelligence systems, can be applied for estimating the temporal changes in the physiological data and in the derived variables at different scales (resolutions). Further implementation of the multi-scale analysis is possible to provide detailed characterization of serial changes using a fuzzy logic classifier or a dynamic neural network with at least one neuron (unit) analyzing changes in one or more states of activity of at least one physiological, biochemical, biophysical, mechanical, or genetic system relative to at least one reference value. For example, such a system could be used to examine changes in activities of the sympathetic and parasympathetic nervous systems over short or long periods of time during sleep, physical, or psychological tests. As another example, the above-described system could be used to characterize dynamics of a chronic disease, such as congestive heart failure, first, by analyzing changes in each physiological indicator (such as heart rate, blood pressure, or cardiac output) at rest and during various physical activities in comparison with individual reference values (Scale I, II), and second, by combining the results of Scale-I-and-II-analyses into a general assessment of changes in the patient's condition (Scale III). Furthermore, the reference values could be represented either by a single parameter or by a relation (mathematical function or statistical distribution) between said reference values and a state or states of physiological, biochemical, biophysical, mechanical, or genetic system. For instance, a reference value could represent a range of changes in a physiological parameter, such as heart rate, over 24 hours or during a stress test. Although these methods are substantially different from each other, a novel, unifying feature of the present invention is that the information is processed at different scales (levels of resolution or details) and that the different levels of processing can be distributed among computers and devices on a network. Thus, in a framework of the present invention, each of the above-described methods could be implemented instead of the linear orthogonal decomposition for multi-scale distributed analysis of physiological data, exchange of the results between the scales, and representation of the results of multi-scale analysis for lay people and medical professionals.

In particular, an artificial intelligence system (an expert system or a neural network) can be implemented using a multi-layer structure, in which each layer of processing rules or nodes (elementary units on the neural net or objects in the expert system) has a different processing resolution (scale). Thus, this structure can have a low-resolution processing (Scale I) and a higher-resolution processing scheme (Scales II and III), as described by the present invention. Such artificial intelligence systems could be used for the types of physiological data that could be modeled by inter-connected nodes with elementary input and output operations (a neural network) or could be represented by informal (heuristic) rules of processing (an expert system), or could be implemented in a combined system of rules and nodes (a hybrid system). Although these methods are very general and widely used in different applications, the present invention describes a novel multi-resolution (multi-scale) structure of these systems and its applications for dynamic analysis of subtle changes in health data.

As another example, Mahalanobis distance, a measure of distance between two points in the space defined by two or more, possibly, correlated variables can be used to determine the probability of a change in the physiological data at different scales. For each variable, the location of the point mean steady-state value (centroid 1) and the mean unsteady value (centroid 2) are determined. Mahalanobis distances from the steady-state and the unsteady centroids to each data point are then calculated. The probability that a point belongs to the steady-state or the unsteady sector is proportional to the Mahalanobis distance from that sector centroid. These distances, for example, could be used for the estimation of temporal changes in electrocardiographic T-wave amplitude shown in FIG. 13. In particular, the probability of a change in the new T-wave amplitude data at a low-resolution scale can be determined using Mahalanobis distance between the new data and the two centroids (steady-state and unsteady one). At the higher-resolution scale, the probability of a change, its magnitude, and other characteristics could be estimated more precisely by separating the steady-state and the unsteady sectors into sub-sectors, determining the corresponding centroids, and estimating Mahalanobis distances between the new data and the centroid of each sub-sector. The locations of the centroids are updated after the new data are collected to provide time-adjusted, individual reference or baseline values. The distances between the centroids demonstrate the individual range of variations in the studied variables, which can be compared to the average values in a group or a population. Mahalanobis distances can also be used to estimate the changes in combinations of variables.

This procedure is similar to the inclusion of additional dimensions (components) into the PCA. However, unlike PCA, the nonlinear estimation or an artificial intelligence approach is not limited to orthogonal components and metric distances, but may include non-orthogonal components (also referred to as the independent components) and nonlinear estimators.

It is therefore seen that this invention provides a physiological data analysis system and method for detecting a plurality of primary elements and comparing the detected elements with reference or baseline values both quantitatively and qualitatively. The outputs from the system in both low level resolution and higher levels of resolution can be understood by both lay persons and medical professionals. The system includes means for exchanging information and direction from an external computer for analysis and modification of the low resolution analysis of the signal.

Whereas particular aspects of the method of the present invention and particular embodiments of the invention have been described for purposes of illustration, it will be appreciated by those skilled in the art that numerous variations of the details may be made without departing from the invention as described in the appended claims.

What is claimed is:

1. A method for analysis of physiological or health data in at least two levels of detail, said method comprising:

analyzing at least one of a plurality of primary elements in said data in first scale, low level resolution to detect one-time changes in such primary elements and thereby identify any abnormal or unstable primary elements by comparing said primary elements with at least one reference value for said at least one of a plurality of primary elements;

analyzing said at least one of a plurality of primary elements in said data in a second scale, higher level resolution using at least one of the following methods selected from mathematical decomposition, time-series analysis, mathematical modeling, computer modeling, signal processing, statistical analysis, and methods of artificial intelligence, and a combination of mathematical decomposition with methods of artificial intelligence to provide detailed characterization of serial changes in any abnormal or unstable primary elements; and exchanging information between said analyzing in said first and second levels of resolution to improve at least one of said first and second analyses.

2. A method as set forth in claim 1 in which said analyzing a plurality of primary elements in said data in first-scale low resolution is selected from at least one of mathematical decomposition, mathematical modeling, computer modeling, time-series analysis, signal processing, statistical analysis, and methods of artificial intelligence.

3. A method as set forth in claim 1 in which analyzing said data to provide detailed characterization of serial changes in said abnormal or unstable primary elements is performed using at least one of the following methods selected from orthogonal decomposition, non-orthogonal decomposition (independent component analysis), multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability and Mahalanobis distance, pattern recognition, fuzzy logic, neural networks, expert systems, and hybrid artificial intelligence systems.

4. A method as set forth in claim 1 in which analyzing said data to provide detailed characterization of serial changes in said abnormal or unstable primary elements is selected from a fuzzy-logic classifier and a dynamic neural network with at least one neuron (unit) analyzing changes in at least one state of activity of at least one physiological, biochemical, biophysical, mechanical, and genetic system relative to at least one reference value.

5. A method as set forth in claim 1 in which said reference values are represented by a relation (function, distribution) between said reference values and at least one state of at least one physiological, biochemical, biophysical, mechanical, and genetic system.

6. A method as set forth in claim 1, in which said analysis and representation are applied to physiological signals selected from at least one of blood pressure, cardiac output, vascular activity, temperature, respiration, cardiac, abdominal, or breathing sounds, blood flow, hormonal concentration, enzyme and protein level, genetic, proteomic, and molecular data, neural activity, electroencephalographic activity, and other electrical, mechanic, sonic, biochemical, biophysical processes in the human body, demographic, psychological, and environmental data.

7. A method as set forth in claim 1, in which the analysis is applied for at least one of improved detection of changes during one-time examination, assessment of short-term and long term dynamics, assessment of fitness level, disease progression, treatment, complications and side-effects control, physical examination, early detection of subtle changes, and timely initiation or adjustment of therapy, early prediction and prevention of physiological disorders and abnormalities, comparison of the values of data obtained from individual patients against averages of values obtained from a group of patients or population of patients to facilitate analysis of individual data and to determine the values that characterize groups of patients with similar characteristics and similar disorders.

8. A method as set forth in claim 1 in which said at least one reference value is selected from preset default reference values, computed reference values previously generated, and manually edited reference values.

9. A system for detection of serial changes in physiological or health data and analysis in at least two levels of detail, said system comprising:
at least one acquisition unit for collecting physiological or health data from a subject over a period of at least several seconds;
at least one first analysis and processing unit for detecting at least one of a plurality of primary elements from said data and processing said primary elements in low level resolution to generate data respecting and comparing at least one reference value respecting said primary elements with data newly received by said first analysis and processing unit and producing at least one indicator respecting any differences between said at least one reference value and said newly received data;
at least one storage unit for storing said at least one reference value respecting said primary elements, and
a communications unit for sending data of said primary elements to at least one computer device for processing and detailed analysis of serial changes in at least some of the said primary elements in said data for a higher resolution analysis using at least one of the methods selected from mathematical decomposition, mathematical modeling, computer modeling, signal processing, time series analysis, statistical analysis, and methods of artificial intelligence for assessing small changes in serial data and for exchanging information with said first analysis and processing unit to improve at least one of said low-level and higher-level resolution.

10. A detection and analysis system as set forth in claim 9 which includes multiple first analysis and processing units connected to at least one computer device.

11. A detection and analysis system as set forth in claim 9 in which said first analysis and processing unit and said at least one computer device analyze said data to provide detailed characterization of serial changes in said abnormal or unstable primary elements using at least one of the following methods selected from orthogonal decomposition, non-orthogonal decomposition (independent component analysis), mathematical modeling, computer modeling, signal processing, time-series analysis, statistical analysis, multidimensional scaling based on non-metric distances and mapping techniques, non-orthogonal linear mappings, nonlinear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability and Mahalanobis distance, pattern recognition, fuzzy logic, neural networks, expert systems, and hybrid artificial intelligence systems.

12. A detection and analysis system as set forth in claim 9 in which at least one of said first analysis and processing unit and said at least one computer device analyze other physiological data selected from at least one of blood pressure, cardiac output, vascular activity, temperature, respiration, cardiac, abdominal, or breathing sounds, blood flow, hormonal concentration, enzyme and protein level, genetic, proteomic, and molecular data, neural activity, electroencephalographic activity, and other electrical, mechanic, sonic, biochemical, biophysical processes in the human body, demographic, psychological, and environmental data.

13. A detection and analysis system as set forth in claim 9 in which said communication unit is wireless.

14. A system as set forth in claim 9 in which said higher-level analysis is distributed among several computers connected via computer networks.

15. A system as set forth in claim 9 in which said data acquisition and low-level analysis of health data are distributed among several personal devices, selected from noninvasive and implantable devices, which are connected via computer networks.

16. A system as set forth in claim 9 in which said at least one computer device is adapted to perform said higher-level analysis of health data using parallel processing.

17. A system as set forth in claim 9 in which said higher-level analysis of health data is distributed among several computers connected via specialized computer networks, including networks for home use, work environment, hospital, and transportation.

18. A system as set forth in claim 9 in which said higher-level analysis of health data is distributed among several computers connected via at least one specialized computer network, including networks for tracking serial changes in patients with at least one condition selected from congestive heart failure, coronary artery or ischemic heart disease, cardiac arrhythmias, hypertension, syncope, asthma, diabetes, and other illnesses.

19. A system as set forth in claim 9 in which said at least one computer device is adapted to perform said higher-level analysis of health data integrated into an artificial intelligence system, which includes at least one method selected from an expert system, a neural network and a combination of the methods (a hybrid system).

20. A system as set forth in claim 9 in which said network of computers includes at least one of a fuzzy-logic classifier and a dynamic neural network with at least one neuron (unit) for analyzing changes in at least one state of activity of at least one physiological, biological, biophysical, mechanical and genetic system relative to at least one reference value.

21. A system as set forth in claim 9 in which said reference values are represented by a relation (function, distribution) between said reference values and at least one state of at least one physiological, biochemical, biophysical, mechanical, and genetic system.

22. A system for detection of serial changes as set forth in claim 9, in which said at least one of first analysis and processing unit and said at least one computer device for a higher resolution analysis performs at least one analysis selected from forecasting or prediction of serial changes or trends in physiological or health data, early prediction and prevention of physiological disorders and abnormalities, assessment of short-term and long term dynamics, fitness level, disease progression, treatment, complications and side-effects control, physical examination, early detection of subtle changes, timely initiation of therapy, adjustment of therapy, comparison of the values of data obtained from individual patients against values obtained from at least one of a group of patients and a population of patients to facilitate analysis of individual data and to determine the values that characterize said at least one of a group of patients and a population of patients with similar characteristics and similar disorders.

23. A system as set forth in claim 9 in which said at least one first analysis and processing unit is adapted to select said at least one reference value from preset default reference values, computed reference values previously generated, and manually edited reference values.

24. A system as set forth in claim 9 in which said computer device is selected from a specialized computer, a specialized processor, a personal computer, a computer organizer (PDA), a cell phone, a smart phone, a group of computers connected via at least one of a local network, a wireless network, and the Internet.

25. A system as set forth in claim 9 in which said higher-level analysis of health data is distributed among several computers connected via specialized computer networks, including networks for home use, work environment, hospital, and transportation.

26. A system as set forth in claim 9 in which said at least one computer device is adapted to perform said higher-level analysis of health data is integrated into an artificial intelligence system, which includes at least one method selected from an expert system, a neural network and a combination of the methods (a hybrid system).

27. A system for detection of serial changes as set forth in claim 9, in which at least one of first analysis and processing unit and at least one computer device for a higher resolution analysis performs at least one analysis selected from forecasting or prediction of serial changes or trends in physiological or health data, early prediction and prevention of physiological disorders and abnormalities, assessment of short-term and long term dynamics, fitness level, disease progression, treatment, complications and side-effects control, physical examination, early detection of subtle changes, timely initiation of therapy, adjustment of therapy, comparison of the values of data obtained from individual patients against values obtained from at least one of a group of patients and a population of patients to facilitate analysis of individual data and to determine the values that characterize said at least one of a group of patients and a population of patients with similar characteristics and similar disorders.

28. A portable system for monitoring physiological or health data and analyzing the data in at least two levels of detail (or resolution), said portable system comprising:

at least one acquisition unit for receiving physiological or health data generated by monitoring a subject for at least several seconds;

at least one analysis unit for detecting at least one of a plurality of primary elements from said signals to detect one-time changes in such primary elements and thereby identify any abnormal or unstable primary elements, storing said at least one of a plurality of primary elements, comparing at least one of said plurality of primary elements which have been stored with at least one of a plurality of primary elements newly received from said analysis module and producing at least one indicator respecting any differences in the data in low level resolution, and analyzing said at least one of a plurality of primary elements in a higher level of resolution using at least one of the following methods selected from mathematical decomposition, mathematical modeling, signal processing, time-series analysis, statistical analysis and methods of artificial intelligence to provide detailed characterization of serial changes in said abnormal or unstable primary elements in higher level resolution;

an output unit for displaying said at least one indicator; and a communications unit for sending data to at least one computer device for processing, analyzing, and exchanging information between said at least one analysis unit and said at least one computer device to improve functionality of at least one of said one analysis unit.

29. A portable system as set forth in claim 28 which includes multiple acquisition units and multiple analysis units connected to a network of computers.

30. A portable system as set forth in claim 29 in which said at least one analysis unit and said network of computers are adapted to analyze said data in low and higher resolution respectively to provide detailed characterization of serial changes in said abnormal or unstable primary elements using at least one of the following methods selected from orthogonal decomposition, non-orthogonal decomposition, independent component analysis, mathematical modeling, statistical analysis, signal processing, time-series analysis, multidimensional scaling based on non-metric distances and mapping techniques, non-orthogonal linear mappings, non-linear mappings and other methods, that make use of projection, re-scaling (change of variables), methods from the theories of singularities, bifurcations, catastrophes, and dynamical systems, and other statistical estimators, such as linear and nonlinear correlation, analysis of variance, cluster analysis, factor analysis, canonical analysis, regression and discriminant function analyses, and probabilistic methods Bayesian probability and Mahalanobis distance, pattern recognition, fuzzy logic, neural networks, expert systems, and hybrid artificial intelligence systems.

31. A portable system as set forth in claim 28 that further includes an analysis unit for analyzing said primary elements in third level high resolution using at least one of the methods selected from mathematical decomposition, mathematical modeling, statistical analysis, signal processing, time-series analysis, and methods of artificial intelligence.

32. A portable system as set forth in claim 28 in which said at least one analysis unit is connected to a network of computers which are adapted to analyze at least one type of physiological data selected from blood pressure, cardiac output, vascular activity, temperature, respiration, cardiac, abdominal, or breathing sounds, blood flow, hormonal concentration, enzyme and protein level, genetic, proteomic, and molecular data, neural activity, electroencephalographic activity, and other electrical, mechanic, sonic, biochemical, biophysical processes in the human body, demographic, psychological, and environmental data.

33. A system as set forth in claim 28 in which said at least one analysis unit includes at least one of a fuzzy-logic classifier and a dynamic neural network with at least one neuron (unit) for analyzing changes in at least one state of activity of at least one physiological, biological, biophysical, mechanical and genetic system relative to at least one reference value.

34. A system as set forth in claim 28 in which said reference values are represented by a relation (function, distribution) between said reference values and at least one state of at least one physiological, biochemical, biophysical, mechanical, and genetic system.

35. A system as set forth in claim 28 which is adapted to use at least two processes selected from electrocardiographic examination of resting electrocardiogram, stress-test, ambulatory (Holter), event, loop-recorded electrocardiogram, and processes for measuring glucose, blood pressure, cardiac output, vascular activity, temperature, respiration, cardiac, abdominal, or breathing sounds, blood flow, hormonal concentration, enzyme and protein level, genetic, proteomic, and molecular data, neural activity, electroencephalographic activity, and other electrical, mechanic, sonic, biochemical, biophysical processes in the human body, demographic, psychological and environmental data.

36. A system as set forth in claim 28 in which said computer device is selected from a specialized computer, a specialized processor, a personal computer, a computer organizer (PDA), a cell phone, a smart phone, a group of computers connected via at least one of a local network, a wireless network, and the Internet.

37. A system for detection of serial changes in health data and analysis of the data, said system comprising:
at least one implantable acquisition unit;
at least one external unit selected from a personal computer, a specialized processor, a personal digital assistant, and a computer organizer for collecting health data from a subject; said an external processing unit having wireless communication with said implantable acquisition unit;
wherein said at least one of said implantable acquisition unit and said external unit have the capability of detecting a plurality of primary elements from said data and processing said primary elements to generate data respecting said primary elements, storing said data respecting said primary elements, comparing data newly received by said implantable acquisition unit with at least one reference value selected from at least one of said data which has been stored (threshold data), manually adjusted threshold data and preset default reference values using at least one of the following methods selected from methods of mathematical decomposition, mathematical modeling, artificial intelligence, statistical analysis, signal processing, time-series analysis, and mathematical decomposition to generate health data of differences between said reference data and said newly received data.

38. A system for detection of serial changes in health data and analysis of the data as set forth in claim 37, in which an implantable acquisition unit includes processing capability.

39. A system as set forth in claim 37 in which said at least one implantable acquisition unit and said at least one external unit have the capability of using at least one method selected from orthogonal decomposition, non-orthogonal decomposition or independent component analysis, multidimensional scaling based on non-metric distances and mapping techniques, non-orthogonal linear mappings, non-linear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability and Mahalanobis distance, pattern recognition, fuzzy logic, neural networks, expert systems, and hybrid artificial intelligence systems.

40. A system as set forth in claim 37 in which said health data may include at least one of blood pressure, cardiac output, vascular activity, temperature, respiration, cardiac, abdominal, or breathing sounds, blood flow, hormonal concentration, enzyme and protein level, genetic, proteomic, and molecular data, neural activity, electroencephalographic activity, and other electrical, mechanic, sonic, biochemical, biophysical processes in the human body, demographic, psychological and environmental data.

41. A system for detection of serial changes in physiological or health data and analysis in at least two levels of detail, said system comprising:
   at least one acquisition unit connected to at least one computer device for collecting physiological or health data from a subject over a period of at least several seconds;
   at least one first analysis and processing unit for detecting at least one of a plurality of primary elements from said data and processing said at least one of a plurality of primary element in low level resolution to generate data respecting said primary elements, and comparing at least one reference value with data newly received by said first analysis and processing unit and producing at least one type of indicator of differences between said at least one reference value and said newly received data;
   at least one storage unit for storing said at least one reference value respecting said primary elements selected from among data previously generated by said at least one first analysis and processing unit (threshold values), manually adjusted threshold values, and preset default values;
   a communications unit for sending data respecting at least one of said plurality of primary elements to at least one computer device for processing and detailed analysis of serial changes in at least one of the said primary elements in said data, said at least one computer device for a higher resolution analysis using at least one method analysis for assessing small changes in serial data and for exchanging information with said first analysis and processing unit to improve at least one of said low-level and higher-level resolution.

42. A detection and analysis system as set forth in claim 41 in which said method of analysis by said at least one computer device uses at least one of mathematical decomposition, time-series analysis, mathematical modeling, signal processing, statistical analysis, methods of artificial intelligence, and combinations of at least two such methods.

43. A detection and analysis system as set forth in claim 41 in which said at least one type of indicator is selected from qualitative indicators and quantitative data indicators.

44. A system for detection of serial changes in physiological or health data and analysis in at least two levels of detail, said system comprising:
   at least one acquisition unit for collecting physiological or health data from a subject over a period of at least several seconds;
   at least one first analysis and processing unit for detecting at least one of a plurality of primary elements from said data and processing said at least one of a plurality of primary elements in low level resolution to generate data respecting said primary elements, and comparing data received by said first analysis and processing unit with at least one reference value to produce at least one indicator respecting any differences between said newly received data and said at least one reference value; and
   a communications unit for sending said at least one type of data selected from among said qualitative indicators, said quantitative data, said physiological data and said health data to at least one computer device for processing and detailed higher level analysis of serial changes in at least some of the said primary elements in said data using at least one of the methods selected from mathematical decomposition, mathematical modeling, computer modeling, signal processing, time-series analysis, statistical analysis, and methods of artificial intelligence for assessing small changes in serial data and for exchanging information with said first analysis and processing unit to improve at least one of said low-level and higher-level resolution.

45. A system as set forth in claim 44 that includes an output unit for displaying said at least one indicator.

46. A system as set forth in claim 44 in which said computer device is selected from a specialized computer, a personal computer, a computer organizer (PDA), a cell phone, a smart phone, a group of computers connected via at least one of a local network and the Internet.

47. A system as set forth in claim 44 in which said reference value is selected from at least one of qualitative indicators, qualitative values, qualitative indicators that have been manually edited, quantitative values that have been manually edited, and preset default values.

48. A system for at least one of monitoring and discrete examination of physiological or health data using at least two levels (resolutions) of processing, said system comprising:
   at least one acquisition unit for collecting data from a subject over a period of at least several seconds; and
   at least one processing (analysis) unit for processing said data with respect to at least one of a plurality of primary elements (referred to as low resolution analysis) and for further processing said data with respect to at least one, and preferably, a plurality of primary elements, including serial changes in said at least one primary element (referred to as higher resolution analysis).

49. A system as set forth in claim 48 which includes at least two processing units, one of which performs said low resolution analysis and another which performs higher resolution analysis, and further includes a communications unit for exchanging information between said low resolution analysis and said higher resolution analysis.

50. A detection and analysis system as set forth in claim 48 which includes multiple first analysis and processing units connected to at least one computer device.

51. A detection and analysis system as set forth in claim 48 in which said first analysis and processing unit and said at least one computer device analyze said data to provide detailed characterization of serial changes in said abnormal or unstable primary elements using at least one of the following methods selected from orthogonal decomposition, non-orthogonal decomposition (independent component analysis), mathematical modeling, computer modeling, signal processing, time-series analysis, statistical analysis, multidimensional scaling based on non-metric distances and mapping techniques, non-orthogonal linear mappings, non-linear mappings and other methods, that make use of projection, re-scaling (change of variables), methods from the theories of singularities, bifurcations, catastrophes, and dynamical systems, and other statistical estimators, linear and nonlinear correlation, analysis of variance, cluster analysis, factor analysis, canonical analysis, regression and discriminant function analyses, and probabilistic methods, Bayesian probability and Mahalanobis distance, pattern recognition, fuzzy logic, neural networks, expert systems, and hybrid artificial intelligence systems.

52. A detection and analysis system as set forth in claim 48 in which at least one of said first analysis and processing unit and said at least one computer device analyze other physiological data selected from at least one of blood pressure, cardiac output, vascular activity, temperature, respiration, cardiac, abdominal, or breathing sounds, blood flow, hormonal concentration, enzyme and protein level, genetic, proteomic, and molecular data, neural activity, electroencephalographic activity, and other electrical, mechanic, sonic, biochemical, biophysical processes in the human body, demographic, psychological, and environmental data.

53. A detection and analysis system as set forth in claim 48 in which said communication unit is wireless.

54. A system as set forth in claim 48 in which said higher-level analysis is distributed among several computers connected via computer networks.

55. A system as set forth in claim 48 in which said data acquisition and low-level analysis of health data are distributed among several personal devices, selected from noninvasive and implantable devices, which are connected via computer networks.

56. A system as set forth in claim 48 in which said at least one first analysis and processing unit is adapted to select said at least one reference value from preset default reference values, computed reference values previously generated, and manually edited reference values.

57. A system as set forth in claim 48 in which said at least one processing unit is selected from a specialized computer, a specialized processor, a personal computer, a computer organizer (PDA), a cell phone, a smart phone, a group of computers connected via at least one of a local network, a wireless network, and the Internet.

58. A system as set forth in claim 48 which has the capability of providing an indication (alarm) in at least one form of a qualitative indicator, data, visualized on a display, sound, and vibration.

59. A system for at least one of monitoring and discrete examination of physiological or health data using at least two levels (resolutions) of processing, said system comprising:

at least one acquisition unit for collecting data from a subject over a period of at least several seconds;

a first processing (analysis) unit for detecting at least one of a plurality of primary elements from said data and processing said at least one of a plurality of primary elements (referred to as low resolution analysis) to generate data respecting said at least one of a plurality of primary elements;

at least one storage unit for storing at least one reference value of said plurality of primary elements;

a comparative unit for comparing said at least one reference value with data newly received from said first analysis and processing unit;

a second processing (analysis) unit (referred to as higher resolution analysis); and a communications unit for exchanging information between said processing in low resolution and said higher resolution processing.

* * * * *